United States Patent
Zhong et al.

(10) Patent No.: US 10,338,179 B2
(45) Date of Patent: Jul. 2, 2019

(54) MAGNETIC RESONANCE METHOD AND APPARATUS FOR QUANTITATIVE TIME-RESOLVED ASSESSMENT OF TISSUE DISPLACEMENT AND RELATED BIOMARKER PARAMETERS WITH BLOOD SUPPRESSION IN THE WHOLE CARDIAC CYCLE

(71) Applicants: Siemens Healthcare GmbH, Erlangen (DE); Emory University, Atlanta, GA (US)

(72) Inventors: Xiaodong Zhong, Marietta, GA (US); John Oshinski, Decatur, GA (US); Deqiang Qiu, Brookhaven, GA (US); Amit Saindane, Decatur, GA (US)

(73) Assignees: Siemens Healthcare GmbH, Erlangen (DE); Emory University, Atlanta, GA (US)

( * ) Notice: Subject to any disclaimer, the term of this patent is extended or adjusted under 35 U.S.C. 154(b) by 807 days.

(21) Appl. No.: 15/045,281

(22) Filed: Feb. 17, 2016

(65) Prior Publication Data

US 2017/0231522 A1 Aug. 17, 2017

(51) Int. Cl.
*A61B 5/055* (2006.01)
*G01R 33/563* (2006.01)
(Continued)

(52) U.S. Cl.
CPC ... *G01R 33/56325* (2013.01); *G01R 33/5607* (2013.01); *A61B 5/7285* (2013.01);
(Continued)

(58) Field of Classification Search
CPC ........... G01R 33/5614; G01R 33/5607; G01R 33/56325; G01R 33/5673; G01R 33/5676; A61B 5/7285
See application file for complete search history.

(56) References Cited

U.S. PATENT DOCUMENTS

| | | | | |
|---|---|---|---|---|
| 5,000,182 A | * | 3/1991 | Hinks | A61B 5/0456 600/413 |
| 6,526,307 B2 | * | 2/2003 | Foo | G01R 33/5601 600/413 |

(Continued)

OTHER PUBLICATIONS

Korosoglou, Grigorios, et al. "Strain-encoded cardiac MR during high-dose dobutamine stress testing: Comparison to cine imaging and to myocardial tagging." Journal of Magnetic Resonance Imaging 29.5 (2009): 1053-1061.

(Continued)

*Primary Examiner* — Steve Rowland

(57) ABSTRACT

Embodiments relate to acquiring magnetic resonance (MR) images with suppressed residual blood signal in the early cardiac phases, leading to images with a preferred dark-blood appearance throughout the entire cardiac cycle, which improves accuracy of subsequent post-processing algorithms. The acquisition of the desired blood suppressed tissue images is achieved through a double inversion recovery pulse in DENSE sequences. The double inversion recovery pulse is applied after an electrocardiogram (ECG) trigger at a beginning point of a repetition time period, followed by a displacement encoding module at an inversion time during the repetition time period and a readout module comprised of a plurality of frames during a remainder of the repetition time period. The displacement encoding module applies a labelling process on the tissue, while the readout module applies an un-labelling process. The readout module comprises an imaging sequence adapted to acquire DENSE images.

18 Claims, 8 Drawing Sheets
(1 of 8 Drawing Sheet(s) Filed in Color)

(51) Int. Cl.
*G01R 33/56* (2006.01)
*A61B 5/00* (2006.01)
*G01R 33/561* (2006.01)
*G01R 33/567* (2006.01)

(52) U.S. Cl.
CPC ...... *G01R 33/5614* (2013.01); *G01R 33/5673* (2013.01); *G01R 33/5676* (2013.01)

(56) References Cited

U.S. PATENT DOCUMENTS

| | | | | |
|---|---|---|---|---|
| 7,835,783 | B1* | 11/2010 | Aletras | G01R 33/56333 324/307 |
| 2002/0188190 | A1* | 12/2002 | Kassai | A61B 5/7285 600/410 |
| 2004/0059213 | A1* | 3/2004 | Kassai | A61B 5/055 600/410 |
| 2008/0015428 | A1* | 1/2008 | Epstein | G06T 7/215 600/410 |
| 2010/0191099 | A1* | 7/2010 | Salerno | A61B 5/055 600/420 |
| 2012/0101367 | A1* | 4/2012 | Kim | A61B 5/055 600/413 |
| 2017/0219672 | A1* | 8/2017 | Miyazaki | G01R 33/4816 |

OTHER PUBLICATIONS

Bansal, Manish, et al. "Feasibility and accuracy of different techniques of two-dimensional speckle based strain and validation with harmonic phase magnetic resonance imaging." Journal of the American Society of Echocardiography 21.12 (2008): 1318-1325.
Setser, Randolph M., et al. "Left ventricular torsional mechanics after left ventricular reconstruction surgery for ischemic cardiomyopathy." The Journal of thoracic and cardiovascular surgery 134.4 (2007): 888-896.
Setser, Randolph M., et al. "Noninvasive assessment of cardiac mechanics and clinical outcome after partial left ventriculectomy." The Annals of thoracic surgery 765 (2003): 1576-1585.
Kramer, Christopher M., et al. "Reverse remodeling and improved regional function after repair of left ventricular aneurysm." The Journal of thoracic and cardiovascular surgery 123.4 (2002): 700-706.
Bilchick, Kenneth C., et al. "Cardiac magnetic resonance assessment of dyssynchrony and myocardial scar predicts function class improvement following cardiac resynchronization therapy." JACC: Cardiovascular Imaging 1.5 (2008): 561-568.
Curry, Cecilia W., et al. "Mechanical dyssynchrony in dilated cardiomyopathy with intraventricular conduction delay as depicted by 3D tagged magnetic resonance imaging." Circulation 101.1 (2000): e2-e2.
Suever, Jonathan D., et al. "Relationship between mechanical dyssynchrony and intra-operative electrical delay times in patients undergoing cardiac resynchronization therapy." Journal of Cardiovascular Magnetic Resonance 16.1 (2014): 4.
Amado, Luciano C., et al. "Multimodality noninvasive imaging demonstrates in vivo cardiac regeneration after mesenchymal stem cell therapy." Journal of the American College of Cardiology 48.10 (2006): 2116-2124.
Haraldsson, Henrik, et al. "Feasibility of asymmetric stretch assessment in the ascending aortic wall with DENSE cardiovascular magnetic resonance." J Cardiovasc Magn Reson 16.6 (2014).
Aletras, Anthony H., et al. "DENSE: displacement encoding with stimulated echoes in cardiac functional MRI." Journal of Magnetic Resonance 137.1 (1999): 247-252.
Kim, Daniel, et al. "Myocardial Tissue Tracking with Two-dimensional Cine Displacement-encoded MR Imaging: Development and Initial Evaluation 1." Radiology 230.3 (2004): 862-871.
Zhong, Xiaodong, et al. "Imaging three-dimensional myocardial mechanics using navigator-gated volumetric spiral cine DENSE MRI." Magnetic Resonance in Medicine 64.4 (2010): 1089-1097.
Zhong, Xiaodong, et al. "Comprehensive cardiovascular magnetic resonance of myocardial mechanics in mice using three-dimensional cine DENSE." J Cardiovasc Magn Reson 13 (2011): 83.
Spottiswoode, Bruce S., et al. "Tracking myocardial motion from cine DENSE images using spatiotemporal phase unwrapping and temporal fitting." Medical Imaging, IEEE Transactions on 26.1 (2007): 15-30.
McConnell, M. V., et al. "Comparison of respiratory suppression methods and navigator locations for MR coronary angiography." AJR. American journal of roentgenology 168.5 (1997): 1369-1375.
Hofman, Mark BM, et al. "MRI of coronary arteries: 2D breath-hold vs 3D respiratory-gated acquisition." Journal of computer assisted tomography 19 (1995): 56-56.
Wang, Yi, et al. "Navigator-echo-based real-time respiratory gating and triggering for reduction of respiration effects in three-dimensional coronary MR angiography." Radiology 198.1 (1996): 55-60.
Matt, A. Bernstein, Kevin F. Bernstein, and Xiaohong J. Zhou. "Handbook of MRI pulse sequences." (2004); pp. 606-630.

\* cited by examiner

MAGNETIC RESONANCE METHOD AND APPARATUS FOR QUANTITATIVE TIME-RESOLVED ASSESSMENT OF TISSUE DISPLACEMENT AND RELATED BIOMARKER PARAMETERS WITH BLOOD SUPPRESSION IN THE WHOLE CARDIAC CYCLE

TECHNOLOGY FIELD

The present invention relates generally to acquisition of magnetic resonance images, and more particularly to suppressing a residual blood signal in magnetic resonance images to allow for accurate quantitative time-resolved assessment of tissue displacement and related biomarker parameters.

BACKGROUND

Many diseases influence tissue displacement and related biomarker parameters, such as strain, twist, and torsion. Quantitative assessment of these parameters is of growing importance. Particularly, quantitative imaging of motion and strain in the cardiovascular system is an emerging field as being able to understand and measure the complex moving and contraction patterns of the heart and vessels can be helpful in both research and clinical settings.

Conventional applications include ischemia detection and evaluation of myocardial mechanics related to cardiac surgery. Newer applications include quantifying mechanical dyssynchrony in heart failure and measuring the functional effects of experimental therapies such as stem cell infusion. Other applications outside of the heart include assessment of vessel wall deformation and stretching.

Magnetic resonance imaging (MRI) has been a powerful tool for studying displacement and motion. Displacement Encoding with Stimulated Echoes (DENSE) is an MII technique for quantitative imaging of tissue motion. This technique encodes tissue displacement into the phase of the magnetic resonance (MR) signal. Displacement or motion values can be extracted from the MR phase images for each displacement encoded direction, and combined to generate a displacement map. The displacement values can be further used to calculate the deformation and mechanics indices including but not limited to strain, twist, and torsion. When cine DENSE images are acquired, i.e., DENSE data at multiple cardiac phases, dynamic or time-resolved information about motion patterns can be further evaluated.

It is preferable to have DENSE images free of blood signal inside the left ventricle chambers or the vessel lumen, as the myocardial tissue or vessel wall is typically the region of interest, not the blood as its displacement is too large. In addition, if blood signal exists in the images, the signal can cause difficulties in delineating the boundaries of the myocardial chamber and vessel lumen, leading to errors in the final resultant images.

This document describes a method and apparatus for suppressing the residual blood signal in the early cardiac phases of the cine DENSE images, providing a dark-blood appearance for the entire cardiac cycle, thus allowing for more accurate quantitative time-resolved assessment of tissue displacement and related biomarker parameters.

SUMMARY

Embodiments of the present invention provide a method and system for suppressing a residual blood signal in early cardiac phases of MR images, such as cine DENSE images.

In an embodiment, a method of acquiring cine DENSE images of tissue with suppressed residual blood signal in early cardiac phases comprises: applying, by a processor, a residual blood signal suppression sequence to the tissue, the residual blood signal suppression sequence comprising: inversion recovery pulses after an electrocardiogram (ECG) trigger at a beginning point of a repetition time period, to obtain a magnetization-inverted slice of the tissue; a displacement encoding module at an inversion time during the repetition time period to apply a labelling process on the tissue and excite an imaging slice of tissue thinner than the magnetization-inverted slice; and a readout module comprised of a plurality of frames during a remainder of the repetition time period, to apply an un-labelling process on the imaging slice of tissue, thereby generating DENSE images of tissue with blood suppression within the imaging slice of tissue. A display processor generates data representing the DENSE images of tissue with blood suppression within the imaging slice of tissue. The sequence covers two cardiac cycles defined as the repetition time period; and the inversion time is selected to allow for a blood signal within the imaging slice of tissue to have a zero magnetization level at the inversion time.

According to an embodiment, a system for acquiring cine DENSE images of tissue with suppressed residual blood signal in early cardiac phases comprises one or more processors for applying a residual blood signal suppression sequence to the tissue and generating data representing the DENSE images of tissue with blood suppression within an imaging slice of tissue.

In an embodiment, the inversion recovery pulses comprise two radio-frequency (RF) inversion recovery (IR) pulses; wherein the first RF IR pulse comprises a spatially non-selective pulse and the second RF IR pulses comprises a spatially selective pulse. In an embodiment, the tissue is the myocardial tissue, and the first RF IR pulse inverts magnetization of the myocardium and blood, and the second RF IR pulse restores magnetization in the magnetization-inverted slice of the tissue.

In an embodiment, the residual blood signal suppression sequence further comprises a navigator gating (NAV) module to reduce respiratory motion artifacts in the images during free breathing in data acquisition, wherein the NAV module is applied at an end of each of the two cardiac cycles.

In an embodiment, the readout module comprises an imaging sequence adapted to acquire the DENSE images, wherein the imaging sequence comprises one of echo planar imaging and spiral imaging.

In an embodiment, the displacement encoding module comprises a stimulated-echo acquisition mode (STEAM) kernel.

In an embodiment, the inversion time is based on one or more of field strength, heart rate, tissue and blood longitudinal relaxation time (T1) values.

According to an embodiment, post-processing of the DENSE images of tissue may be performed by a processor, wherein post-processing comprises one or more of phase unwrapping, displacement extraction, tissue tracking, temporal fitting, and mechanics indices calculation.

In an embodiment, the DENSE images of tissue with blood suppression are utilized for quantitative assessment of biomarker parameters of tissue and organ, comprising one or more of mechanical properties parameters and time-resolved dynamic parameters.

BRIEF DESCRIPTION OF THE DRAWINGS

The patent or application file contains at least one drawing executed in color. Copies of this patent or patent application publication with color drawing will be provided by the Office upon request and payment of the necessary fee.

The foregoing and other aspects of the present invention are best understood from the following detailed description when read in connection with the accompanying drawings. For the purpose of illustrating the invention, shown in the drawings are embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Embodiments of the present invention relate to a method and apparatus for suppressing a residual blood signal in early cardiac phases of magnetic resonance (MR) images, such as cine Displacement Encoding with Stimulated Echoes (DENSE) images.

As noted above, DENSE is an MRI technique for quantitative imaging of tissue motion. This technique encodes tissue displacement into the phase of the MR signal. Displacement or motion values can be extracted from the MR phase images for each displacement encoded direction, and combined to generate a displacement map. The displacement values can be further used to calculate the deformation and mechanics indices including but not limited to strain, twist, and torsion. When cine DENSE images are acquired, i.e., DENSE data at multiple cardiac phases, dynamic or time-resolved information about motion patterns can be further evaluated.

Figure 1:
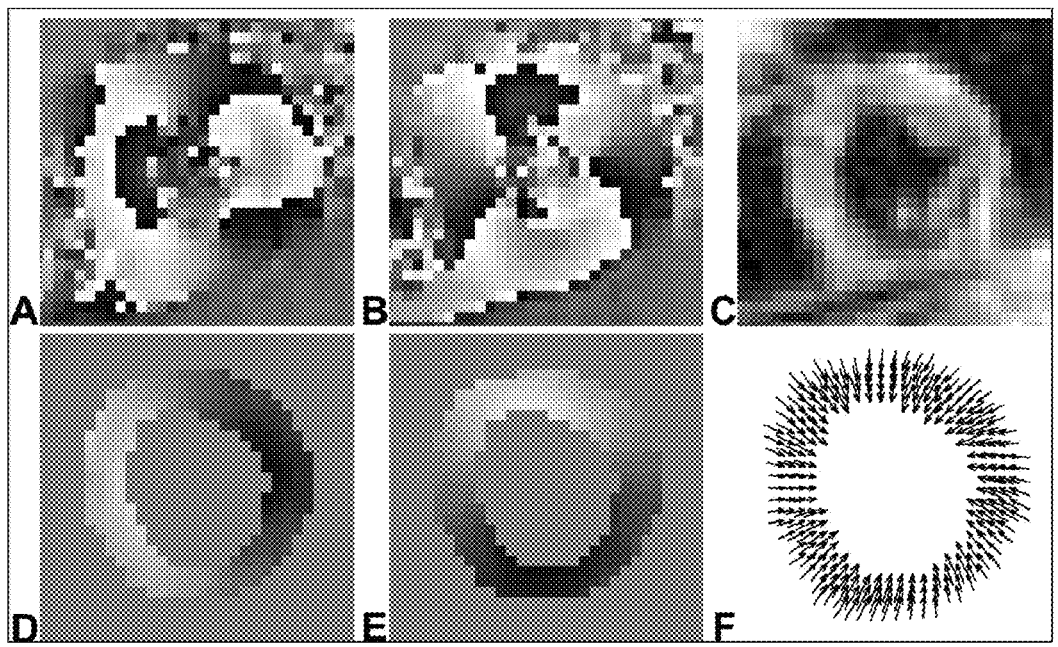
FIG. 1 illustrates example DENSE images and two-dimensional displacement maps of the left ventricle of the heart at end-systole.

With reference to FIG. 1, shown are example DENSE images and the two-dimensional (2D) displacement map of the left ventricle of the heart at end-systole. The left column (A, D) contains the phase images displacement-encoded in the horizontal direction, and the middle column (B, E) contains the phase images displacement-encoded in the vertical direction. The first row contains the phase-reconstructed (A, B) and the magnitude-reconstructed (C) images from the DENSE images acquired directly from the scanner. Phase wrap is seen in the phase-reconstructed images at end-systole (A, B). The second row contains the segmented left ventricle and its unwrapped phase images (D, E) corresponding to (A, B), as well as the resulting 2D displacement map (F).

Figure 2:
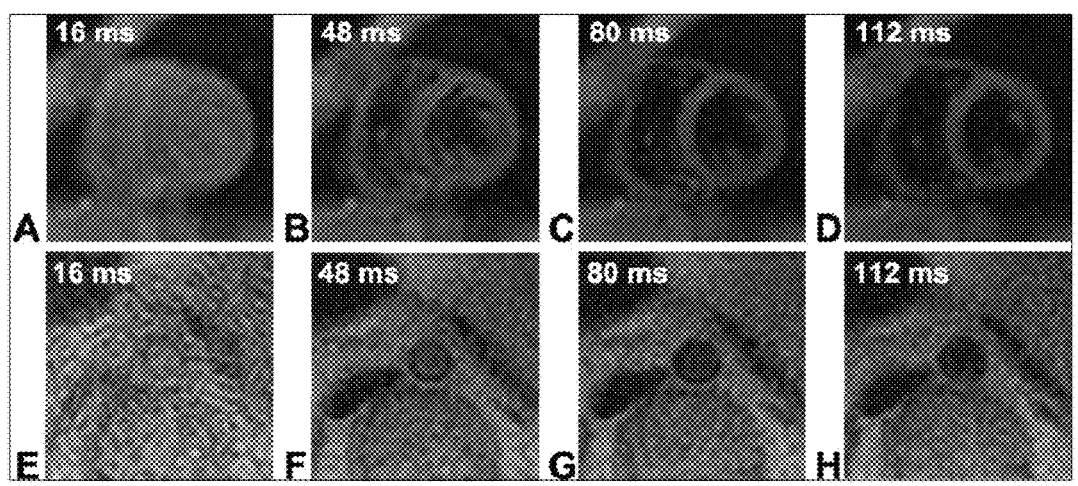
FIG. 2 illustrates example cine DENSE images portraying the blood signal in the left ventricle and in the aorta lumen at the early cardiac phases.

FIG. 2 illustrates example cine DENSE images portraying the blood signal in the left ventricle (top row) and in the aorta lumen (bottom row) at the early cardiac phases. The columns correspond to four consecutive cardiac phases at time of 16, 48, 80, and 112 ms after the ECG R-wave, respectively.

A single-phase DENSE image inherently has dark-blood appearance. This is because the single-phase DENSE image typically has a designed waiting time between the displacement encoding module and the data sampling module. During this waiting time, the blood which went through the displacement encoding applied by the DENSE sequence travels out of the imaging plane when the DENSE data is sampled/acquired and does not contribute to any signal in the resultant DENSE image. However, in the case of cine DENSE, the data of each cardiac phase is acquired as fast as possible, and when the data of the early cardiac phases are acquired, the blood may not yet have traveled out of the imaging plane. The result is that residual blood remains in the left ventricle (A and B in FIG. 2) and in the aorta lumen (E, F, and G in FIG. 2). In contrast, for later cardiac phases (C, D, and H in FIG. 2), the blood signal is mostly not present, and the images have a preferred dark-blood appearance.

Thus, as can be seen from FIG. 2, it is important to suppress the residual blood signal in the early cardiac phases of the cine DENSE images, providing the dark-blood appearance for the entire cardiac cycle. Embodiments disclosed herein accomplish this goal.

Figure 3:
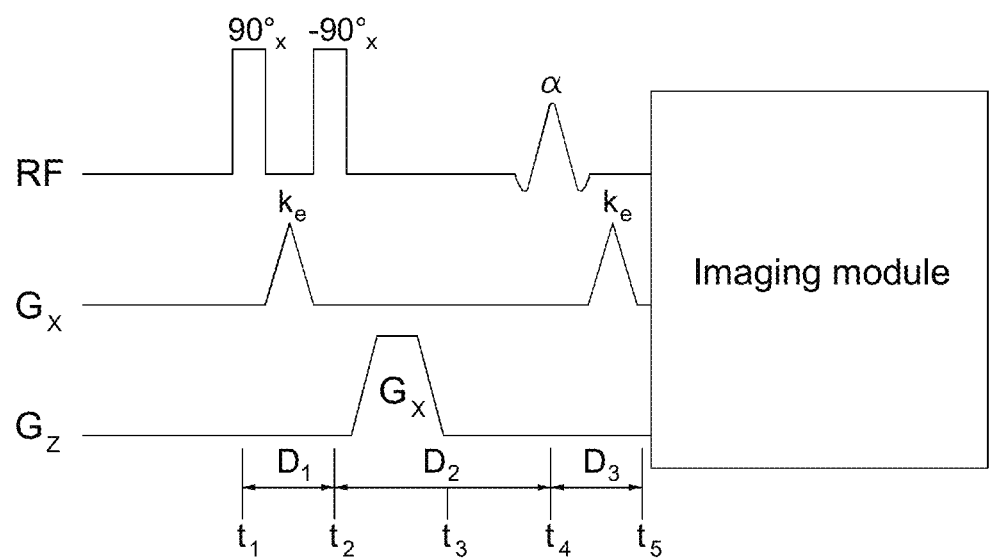
FIG. 3 is a timing diagram of the displacement encoding module in DENSE pulse sequences.

With reference to FIG. 3, an exemplary timing diagram 300 of the displacement encoding module in DENSE pulse sequences, which encodes displacement in the x direction, is shown. RF are the radio-frequency pulses; $G_x$ and $G_z$ are the magnetic gradient field in the x and z direction, respectively. The angle notation $90°_x$ is the rotation about the x-axis by an angle of 90° in the left-hand convention. The RF pulse of $-90°_x$ is accomplished by setting the phase of the RF pulse of $90°_x$ to be 180°. α indicates the rotation about the x-axis by a small flip angle of α. $k_e$ is the spatial frequency imparted by the displacement encoding gradient, which is proportional to the area of the gradient and is given by $$k_e = \frac{\gamma}{2\pi}\int_{t_1}^{t_2} G(\tau)d\tau.$$

$G_s$ is a spoiler gradient. $D_1$-$D_3$ are the time durations, and $t_1$-$t_5$ are the time points.

With continued reference to FIG. 3, the sequence starts with a displacement-encoding module, also referred to as a 1-1 spatial modulation of magnetization (SPAMM) kernel in the tagging sequence, which includes two non-selective 90° RF pulses separated by a displacement-encoding gradient, and followed by a spoiler gradient. This displacement-encoding module can be played out at any time of interest during the cardiac cycle, but is typically done at end-diastole. The displacement-encoding module applies a labelling process on the tissue, which is very similar with the tissue labelling/tagging process in tissue tagging sequences and works with the un-labelling process together to fulfill the purpose of displacement encoding.

The displacement-encoding module is followed by the application of a readout module, which can employ various imaging sequences to sample the k-space after the application of the displacement-decoding gradient, including but not limited to echo planar imaging (EPI) and spiral imaging. This readout module can be adapted to acquire multi-phase or cine data. The flip angle of the slice-selective excitation RF pulse in the readout modules can be either 90° (usually for a single-phase DENSE sequence with only one readout module) or a small flip angle α (usually for the multi-phase or cine DENSE sequence with multiple readout modules), depending on the application. The readout module applies an un-labelling process on the tissue, which works with the previous labelling process in the displacement-encoding module to finish the displacement encoding. An ECG-gated cine DENSE sequence that uses an EPI k-space trajectory is shown in FIG. 4.

Figure 4:
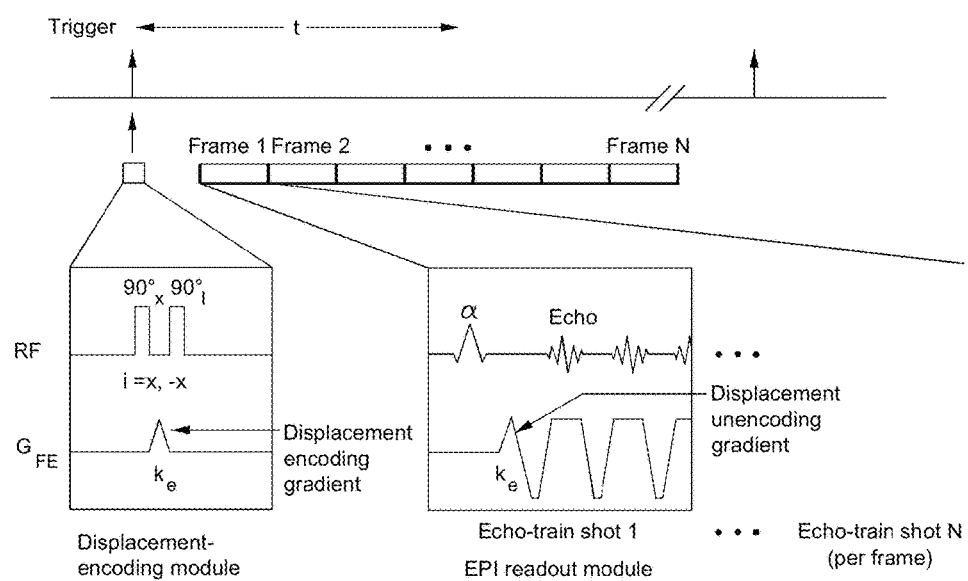
FIG. 4 is a timing diagram of an EPI cine DENSE sequence.

FIG. 4 is a timing diagram 400 of an EPI cine DENSE sequence. In practice, to minimize TE, the displacement unencoding gradients are combined with spatial encoding gradients. The phase of the second 90° RF pulse alters from the x direction to the −x direction, so that a complete dataset for complementary spatial modulation of magnetization (CSPAMM) artifact suppression can be acquired.

Only tissue which underwent both the labelling process in the displacement-encoding module and the un-labelling process in the readout module can contribute to the resultant DENSE data. If the tissue underwent only the labelling process or only the un-labelling process, its signal will be inherently removed by the DENSE signal processing algorithm (for example, the complementary CSPAMM subtraction).

The timing diagrams of FIGS. 3 and 4 are exemplary sequences that may be used in accordance with embodiments disclosed herein. Other sequences known to those of skill in the art may alternatively be used.

According to embodiments provided herein, a dark-blood, inversion recovery DENSE method is capable of quantifying tissue displacement and motion, and evaluating the tissue mechanical properties by calculating indices based on the displacement and motion values. Specifically, this method allows for acquisition of cine DENSE images with suppression of the residual blood signal in the early cardiac phases, providing the dark-blood appearance for the entire cardiac cycle, which improves the accuracy of subsequent post-processing algorithms.

Although embodiments disclosed herein are described with reference to a cine DENSE EPI sequence, other sequence types may alternatively be used. It is straightforward to one of ordinary skill in the art to extend and adapt to other sequence types, including, but not limited to, balanced steady state free precession (balanced SSFP or trueFISP) sequence, and the spiral sequence. In addition, the method disclosed herein can be similarly applied to the single-phase (i.e., non-cine) DENSE sequence, tagging sequence, strain-encoded (SENC) sequence, and other stimulated-echo acquisition mode (STEAM) MRI sequences, to achieve the black blood appearance for the whole cardiac cycle.

According to an embodiment, double inversion recovery pulses in DENSE sequences are utilized to achieve blood signal suppression. An illustration to demonstrate the design and relative timing of the ECG triggering, sequence events, the magnetization changes corresponding to the critical sequence events time points, and the inversion/excitation slice positions, is shown in diagram 500 of FIG. 5. The following description is with reference to the features of FIG. 5.

The repetition time (TR) 510 of the sequence covers two cardiac cycles. Due to the possible length of scan time, which is too long to do breath-hold acquisition, navigator gating (NAV) is used to reduce the respiratory motion artifacts in the image during free breathing in the data acquisition. According to an embodiment, the NAV module 542 is played at the end of each cardiac cycle (or R-R interval), so as not to occupy and interfere with the sequence timing. When both NAVs 542 in the same TR 510 are accepted, the data acquired during this TR 510 is used for the eventual image reconstruction.

"Magnetization" row 560 illustrates magnetization of a tissue signal 562 and a blood signal 564 during the application of the sequence events 540. "Inversion or excitation slice position" row 570 illustrates effects of the sequence events 540 on the image slices.

At a dedicated time point retrospectively determined by the inversion time (TI) 520, two 180° radio-frequency (RF) inversion recovery (IR) pulses 544, 546 in close succession after one ECG trigger 530 are played at the beginning of this specific TR 510. The first IR pulse 544 is spatially non-selective (NS), while the second IR pulse 546 is spatially selective (SS).

Figure 5:
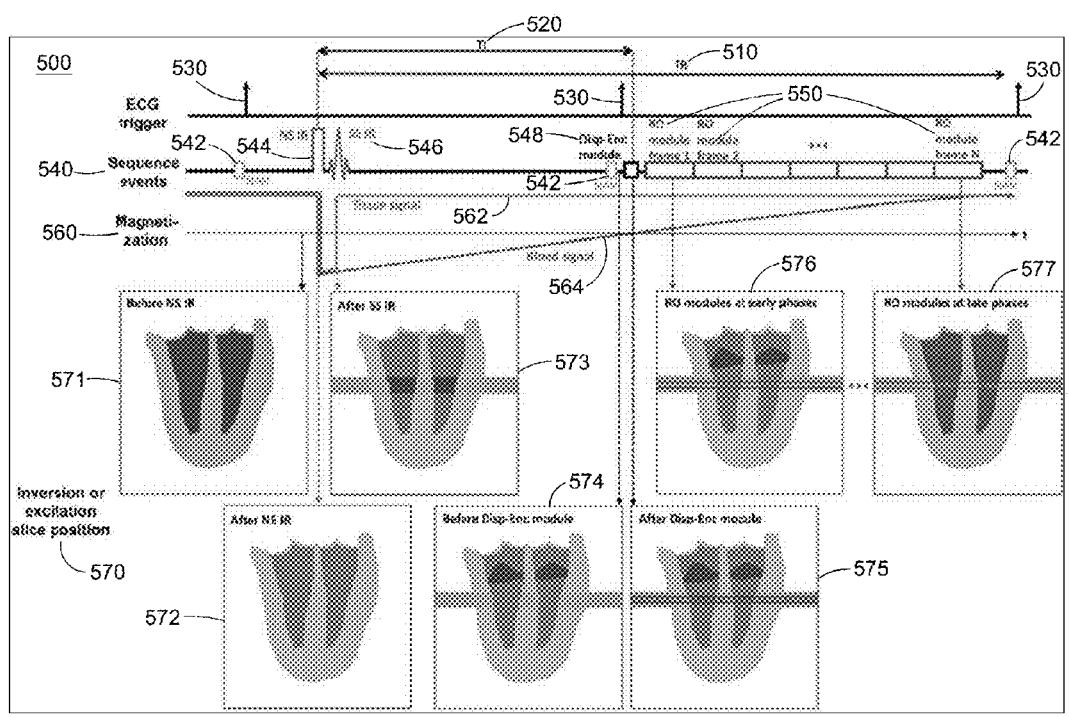
FIG. 5 is an illustration demonstrating design and relative timing of ECG triggering, sequence events, magnetization changes corresponding to critical sequence events time points, and the inversion/excitation slice positions, according to an embodiment.

The first 180° IR pulse 544 inverts all spins within the entire active volume of the transmit coil (the "After NS IR" subplot 572 in the "Inversion or excitation slice position" row 570 in FIG. 5, showing the entire volume with inverted or non-fully-recovered magnetization in gray scale), while the second 180° IR pulse is spatially selective, whose effects are restricted to a single thick slice (the green slice in the "After SS IR" subplot 573 in the "Inversion or excitation slice position" row 570 in FIG. 5). The displacement encoding module 548 excites a slice for imaging thinner than the magnetization-inverted slice of the second 180° IR pulse 546 (the purple box in the "After Disp-Enc module" 575, "RO modules at early phases" 576, and "RO modules at late phases" 577 subplots in the "Inversion or excitation slice position" row 570 in FIG. 5).

With further reference to FIG. 5, before the first 180° IR pulse 544, the magnetization of both myocardium and blood is in the equilibrium stage and is represented in full color as shown in the "Before NS IR" subplot 571. As indicated by both the "Tissue signal" and the "Blood signal" curves (562 and 564, respectively) in the "Magnetization" row 560 and the "After NS IR" subplot 572 in the "Inversion or excitation slice position" row 570 in FIG. 5, the magnetization of both the myocardium and the blood is inverted by the first 180° NS IR pulse 542. The second 180 SS IR pulse 546 restores magnetization of both myocardium and blood to the positive longitudinal axis within the thick slice marked in green (the gray scale on the myocardium and blood within that thick green slice is therefore cleared, as shown in the "After SS IR" subplot 573). It is also noted that the "Tissue signal" magnetization curve 562 within the thick slice marked in green is restored to the positive axis (the "Tissue signal" curve 562 in the "Magnetization" row 560 in FIG. 5), and so is the blood within the thick slice marked in green (the corresponding magnetization curve is not shown in FIG. 5). For myocardium and blood outside the thick slice marked in green, the longitudinal magnetization remains inverted or negative, as shown in the "After SS IR" subplot 573. During the time marked as TI 520, the inverted blood initially outside the thick slice marked in green undergoes T1 (longitudinal relaxation time) recovery, and passes through zero magnetization at the end of TI when a specific TI is selected with care (the "Blood signal" curve 564 marked in blue in the "Magnetization" row 560 in FIG. 5). At the same time, the blood within the thick slice marked in green flows out (illustrated as the two red patches in the "Before Disp-End module" subplot 574 and other subplots (e.g., 575, 576)), and the outside blood flows into and replaces the blood within the thick slice marked in green (illustrated as the gray color within the thick slice marked in green in the "Before Disp-End module" subplot 574). When the displacement encoding module 548 excites a thinner slice for displacement encoding and further imaging, it is equivalent to applying a labelling process on this thinner slice (illustrated as the purple line-shaded box in the "After Disp-End module" subplot 575). Later, at each readout module 550, an equivalent un-labelling process is performed to collaborate with the labelling process so that the wanted DENSE information is generated (illustrated as cleared, no-line-shaded purple box regions as shown in the "RO modules at early phases" subplot 576).

At the time of displacement-encoding module 548, the displacement-encoded magnetization has the myocardium magnetization near equilibrium (the "Tissue signal" curve 562 in the "Magnetization" row 560 in FIG. 5) and the blood magnetization at zero level (the "Blood signal" curve 564 in the "Magnetization" row 560 in FIG. 5). This can also be assumed for the acquisition at early cardiac phases. In addition, for early cardiac phases, the blood within the thinner slice marked with the purple box has not traveled out. As a result, although both the myocardium and the blood within this thinner slice marked with purple box experience both the labelling and the un-labelling processes, only the myocardium tissue signal is preserved and exists in the longitudinal magnetization by the STEAM kernel in the displacement encoding module 548, because the blood in the imaging slice at the early cardiac phases (for example, RO module frame 1, 2, 3, . . . ) would contribute zero or only a little signal due to the zero magnetization, leading to the dark blood appearance (illustrated as the gray blood regions in the no-line-shaded purple box in the "RO modules at early phases" subplot 576). The blood magnetization grows according to T1 recovery during the evolution of the stored longitudinal magnetization (for example, for the RO modules 550 of frame 4, . . . , N), but as observed and mentioned previously, when that happens the blood which underwent the displacement encoding module 548 (the labelling process) usually already travels out of the imaging plane (illustrated as the two purple line-shaded regions out of the purple box in the "RO modules at late phases" subplot 577, which experienced only the labelling process), and the blood which now exists in the imaging slice did not experience the labelling process but only the un-labelling process and therefore does not contribute any signal in the resultant DENSE images (illustrated as the two yellow line-shaded blood regions in the purple box in the "RO modules at late phases" subplot 577, which experienced only the un-labelling process). With these two outcomes led by this carefully designed sequence, cine DENSE images can have the dark blood appearance at both early and late cardiac phases, i.e., blood suppression for the whole cardiac cycle.

The TI needs to be chosen carefully to achieve the aforementioned goal. The optimized value of TI depends on many factors, such as field strength, heart rate, tissue and blood T1 values. For example, for cardiac imaging at 1.5 T with a heart rate of 60 BPM, this typically means a TI of approximately 650 msec. If the heart rate is too fast, TI must be reduced. As a start point to initially set TI, a theoretical equation can be used:

$$TI = T1 \cdot \ln\left(\frac{2}{1 + e^{-TR/T1}}\right).$$

Subsequently, the post-processing of cine DENSE data may include, but is not limited to, the following sequential steps: phase unwrapping, displacement extraction, tissue tracking, temporal fitting, and mechanics indices calculation such as strain, twist, torsion, and dynamic or time-resolved information. The post-processing, after cine DENSE data is acquired according to embodiments described herein, may be carried out according to known methods.

Figure 6:
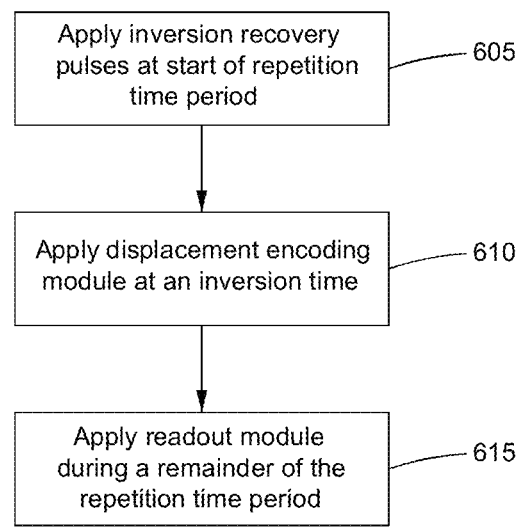
FIG. 6 is a flowchart illustrating a method of acquiring cine DENSE images with suppressed residual blood signal in early cardiac phases, according to embodiments provided herein.

With reference to FIG. 6, a flowchart 600 is provided, illustrating a method of acquiring cine DENSE images of tissue with suppression of residual blood signal in early cardiac phases.

The following sequences are applied to a portion of tissue: at 605, inversion recovery pulses are applied after an ECG trigger at a start of a repetition time period, to obtain a magnetization-inverted slice for imaging of the tissue.

At 610, a displacement-encoding module is applied at an inversion time during the repetition time period, to apply a labelling process on the tissue and excite a slice of tissue for imaging, the slice of tissue for imaging thinner than the magnetization-inverted slice.

At 615, a readout module comprised of a plurality of frames is applied during a remainder of the repetition time, to apply an un-labelling process on the slice of tissue, thereby generating DENSE signals with blood suppression.

Figure 7:
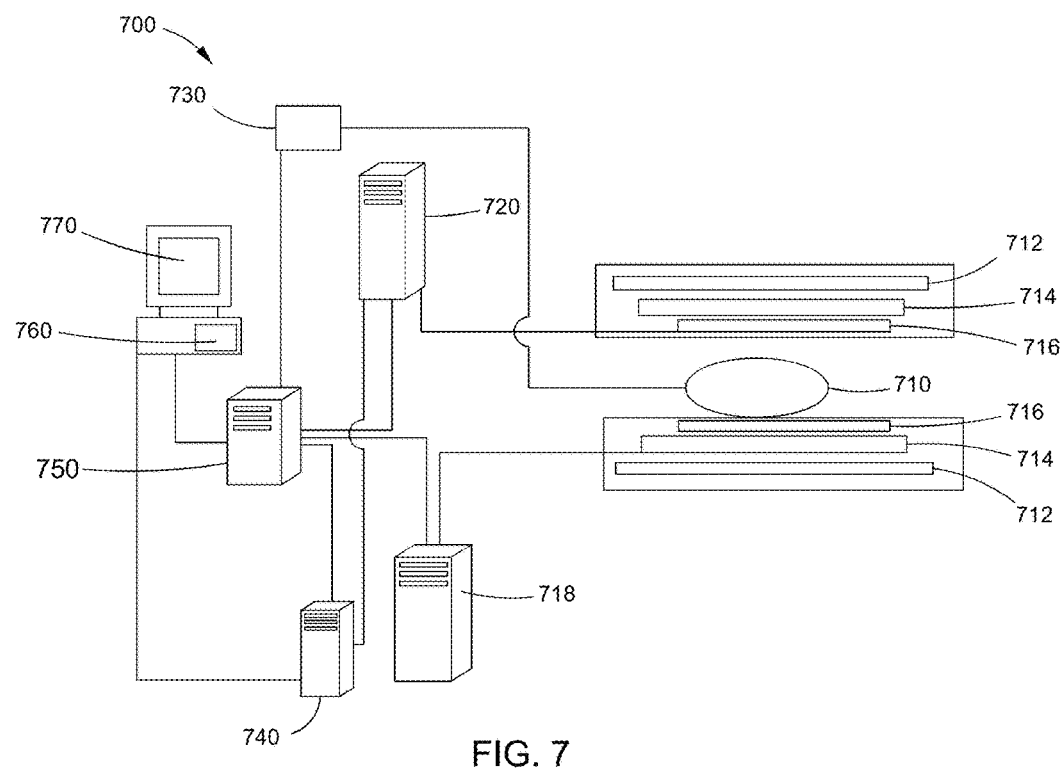
FIG. 7 illustrates a system for suppressing a residual blood signal in early cardiac phases of cine DENSE images, according to embodiments provided herein.

Turning to FIG. 7, a system 700 for acquiring cine DENSE images of tissue with suppression of the residual blood signal in the early cardiac phases is provided. The system 700 includes a source 710 of the tissue, such as a patient. 712, 714, and 716 represent the coils and magnets of an MRI system and are, in an exemplary embodiment, a high field magnet 712, a gradient coil 714, and a radio-frequency (RF) coil 716. Processors 718 (gradient and shim coil controller) and 720 (radio-frequency controller) control the MR magnets and coils. The MRI system components 712, 714, and 716 and processors 718 and 720 depicted in FIG. 7 are one example of an MRI system; other components and processors may be used as known to one of skill in the art to obtain an MR image of tissue.

The system 700 further includes an input processor 730, an image data processor 740, a display processor 760, and an interface 770. A central control system 750 controls the overall operation of and data communication between each of the processors 718, 720, 730, 740, and 760.

Figure 8:
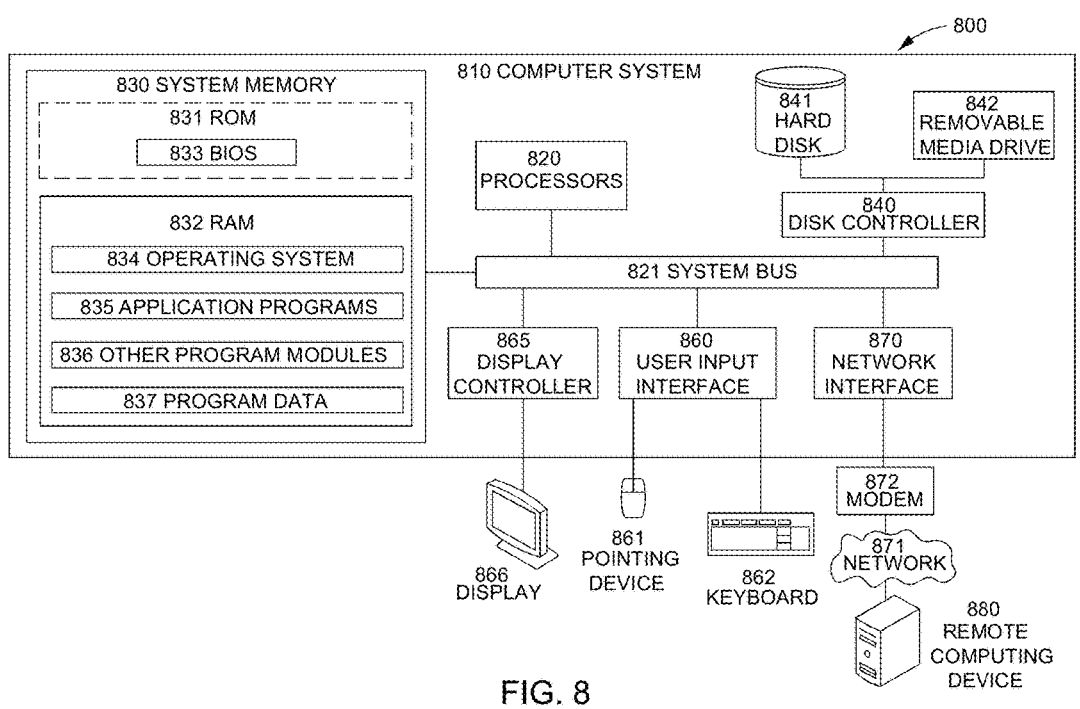
FIG. 8 is an exemplary computing environment in which embodiments disclosed herein may be implemented.

FIG. 8 illustrates an exemplary computing environment 800 within which embodiments of the invention may be implemented. Computing environment 800 may include computer system 810, which is one example of a computing system upon which embodiments of the invention may be implemented. Computers and computing environments, such as computer 810 and computing environment 800, are known to those of skill in the art and thus are described briefly here.

As shown in FIG. 8, the computer system 810 may include a communication mechanism such as a bus 821 or other communication mechanism for communicating information within the computer system 810. The system 810 further includes one or more processors 820 coupled with the bus 821 for processing the information. The processors 820 may include one or more central processing units (CPUs), graphical processing units (GPUs), or any other processor known in the art.

The computer system 810 also includes a system memory 830 coupled to the bus 821 for storing information and instructions to be executed by processors 820. The system memory 830 may include computer readable storage media in the form of volatile and/or nonvolatile memory, such as read only memory (ROM) 831 and/or random access memory (RAM) 832. The system memory RAM 832 may include other dynamic storage device(s) (e.g., dynamic RAM, static RAM, and synchronous DRAM). The system memory ROM 831 may include other static storage device(s) (e.g., programmable ROM, erasable PROM, and electrically erasable PROM). In addition, the system memory 830 may be used for storing temporary variables or other intermediate information during the execution of instructions by the processors 820. A basic input/output system 833 (BIOS) containing the basic routines that help to transfer information between elements within computer system 810, such as during start-up, may be stored in ROM 831. RAM 832 may contain data and/or program modules that are immediately accessible to and/or presently being operated on by the processors 820. System memory 830 may additionally include, for example, operating system 834, application programs 835, other program modules 836 and program data 837.

The computer system 810 also includes a disk controller 840 coupled to the bus 821 to control one or more storage devices for storing information and instructions, such as a magnetic hard disk 841 and a removable media drive 842 (e.g., floppy disk drive, compact disc drive, tape drive, and/or solid state drive). The storage devices may be added to the computer system 810 using an appropriate device interface (e.g., a small computer system interface (SCSI), integrated device electronics (IDE), Universal Serial Bus (USB), or FireWire).

The computer system 810 may also include a display controller 865 coupled to the bus 821 to control a display or monitor 866, such as a cathode ray tube (CRT) or liquid crystal display (LCD), for displaying information to a computer user. The computer system 810 includes an input interface 860 and one or more input devices, such as a keyboard 862 and a pointing device 861, for interacting with a computer user and providing information to the processors 820. The pointing device 861, for example, may be a mouse, a trackball, or a pointing stick for communicating direction information and command selections to the processors 820 and for controlling cursor movement on the display 866. The display 866 may provide a touch screen interface which allows input to supplement or replace the communication of direction information and command selections by the pointing device 861.

The computer system 810 may perform a portion or all of the processing steps of embodiments of the invention in response to the processors 820 executing one or more sequences of one or more instructions contained in a memory, such as the system memory 830. Such instructions may be read into the system memory 830 from another computer readable medium, such as a hard disk 841 or a removable media drive 842. The hard disk 841 may contain one or more datastores and data files used by embodiments of the present invention. Datastore contents and data files may be encrypted to improve security. The processors 820 may also be employed in a multi-processing arrangement to execute the one or more sequences of instructions contained in system memory 830. In alternative embodiments, hard-wired circuitry may be used in place of or in combination with software instructions. Thus, embodiments are not limited to any specific combination of hardware circuitry and software.

As stated above, the computer system 810 may include at least one computer readable medium or memory for holding instructions programmed according to embodiments provided herein and for containing data structures, tables, records, or other data described herein. The term "computer readable medium" as used herein refers to any medium that participates in providing instructions to the processors 820 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 841 or removable media drive 842. Non-limiting examples of volatile media include dynamic memory, such as system memory 830. Non-limiting examples of transmission media include coaxial cables, copper wire, and fiber optics, including the wires that make up the bus 821. Transmission media may also take the form of acoustic or light waves, such as those generated during radio wave and infrared data communications.

The computing environment 800 may further include the computer system 810 operating in a networked environment using logical connections to one or more remote computers, such as remote computer 880. Remote computer 880 may be a personal computer (laptop or desktop), a mobile device, a server, a router, a network PC, a peer device or other common network node, and typically includes many or all of the elements described above relative to computer system 810. When used in a networking environment, computer system 810 may include modem 872 for establishing communications over a network 871, such as the Internet. Modem 872 may be connected to system bus 821 via user network interface 870, or via another appropriate mechanism.

Network 871 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 810 and other computers (e.g., remote computing system 880). The network 871 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 871.

As described herein, the various systems, subsystems, agents, managers and processes can be implemented using hardware components, software components and/or combinations thereof.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A method of acquiring images of tissue with suppression of residual blood signal in early cardiac phases, the method comprising:
   applying, by a processor, a residual blood signal suppression sequence to the tissue, the residual blood signal suppression sequence comprising:
      inversion recovery pulses after an electrocardiogram (ECG) trigger at a beginning point of a repetition time period, to obtain a magnetization-inverted slice of the tissue;
      a displacement encoding module at an inversion time during the repetition time period to apply a labelling process on the tissue and excite an imaging slice of tissue thinner than the magnetization-inverted slice; and
      a readout module comprised of a plurality of frames during a remainder of the repetition time period, to apply an un-labelling process on the imaging slice of tissue, thereby generating cine Displacement Encoding with Stimulated Echoes (DENSE) images of the tissue with blood suppression within the imaging slice of tissue; and
   generating, at a display processor configured to communicate with the processor, data representing the cine DENSE images of the tissue with blood suppression within the imaging slice of tissue;
   wherein the sequence covers two cardiac cycles defined as the repetition time period; and
   wherein the inversion time is selected to allow for a blood signal within the imaging slice of tissue to have a zero magnetization level at the inversion time.

2. The method of claim 1, wherein the inversion recovery pulses comprise two radio-frequency (RF) inversion recovery (IR) pulses;
   wherein the first RF IR pulse comprises a spatially non-selective pulse and the second RF IR pulses comprises a spatially selective pulse.

3. The method of claim 2, wherein the tissue comprises the myocardial tissue, and wherein the first RF IR pulse inverts magnetization of the myocardium and blood; and wherein the second RF IR pulse restores magnetization in the magnetization-inverted slice of the tissue.

4. The method of claim 1, wherein the residual blood signal suppression sequence further comprises a navigator gating (NAV) module to reduce respiratory motion artifacts in the images during free breathing in data acquisition, wherein the NAV module is applied at an end of each of the two cardiac cycles.

5. The method of claim 1, wherein the readout module comprises an imaging sequence adapted to acquire the DENSE images, wherein the imaging sequence comprises one of echo planar imaging and spiral imaging.

6. The method of claim 1, wherein the displacement encoding module comprises a stimulated-echo acquisition mode (STEAM) kernel.

7. The method of claim 1, wherein the inversion time is based on one or more of field strength, heart rate, tissue and blood longitudinal relaxation time (T1) values.

8. The method of claim 1, further comprising post-processing, at an image data processor, the DENSE images of the tissue, wherein post-processing comprises one or more of phase unwrapping, displacement extraction, tissue tracking, temporal fitting, and mechanics indices calculation.

9. The method of claim 1, wherein the DENSE images of the tissue with blood suppression are utilized for quantitative assessment of biomarker parameters of tissue and organ, comprising one or more of mechanical properties parameters and time-resolved dynamic parameters.

10. A system for acquiring images of tissue with suppression of residual blood signal in early cardiac phases, the system comprising:
    a processor configured to apply a residual blood signal suppression sequence to the tissue, the residual blood signal suppression sequence comprising:
       inversion recovery pulses after an electrocardiogram (ECG) trigger at a beginning point of a repetition time period, to obtain a magnetization-inverted slice of the tissue;
       a displacement encoding module at an inversion time during the repetition time period to apply a labelling process on the tissue and excite an imaging slice of tissue thinner than the magnetization-inverted slice; and
       a readout module comprised of a plurality of frames during a remainder of the repetition time period, to apply an un-labelling process on the imaging slice of tissue, thereby generating cine Displacement Encoding with Stimulated Echoes (DENSE) images of the tissue with blood suppression within the imaging slice of tissue; and
    a display processor configured to communicate with the processor to generate data representing the DENSE images of the tissue with blood suppression within the imaging slice of tissue;
    wherein the sequence covers two cardiac cycles defined as the repetition time period; and
    wherein the inversion time is selected to allow for a blood signal within the imaging slice of tissue to have a zero magnetization level at the inversion time.

11. The system of claim 10, wherein the inversion recovery pulses comprise two radio-frequency (RF) inversion recovery (IR) pulses;
    wherein the first RF IR pulse comprises a spatially non-selective pulse and the second RF IR pulses comprises a spatially selective pulse.

12. The system of claim 11, wherein the tissue comprises the myocardial tissue, and wherein the first RF IR pulse inverts magnetization of the myocardium and blood of a whole volume; and wherein the second RF IR pulse restores magnetization in the magnetization-inverted slice for imaging of the tissue.

13. The system of claim 10, wherein the residual blood signal suppression sequence further comprises a navigator gating (NAV) module to reduce respiratory motion artifacts in the images during free breathing in data acquisition, wherein the NAV module is applied at an end of each of the two cardiac cycles.

14. The system of claim 10, wherein the readout module comprises an imaging sequence adapted to acquire the DENSE images, wherein the imaging sequence comprises one of echo planar imaging and spiral imaging.

15. The system of claim 10, wherein the displacement encoding module comprises a stimulated-echo acquisition mode (STEAM) kernel.

16. The system of claim 10, wherein the inversion time is based on one or more of field strength, heart rate, tissue and blood longitudinal relaxation time (T1) values.

17. The system of claim 10, further comprising an image data processor configured to perform post-processing of the DENSE images of the tissue, wherein the post-processing comprises one or more of phase unwrapping, displacement extraction, tissue tracking, temporal fitting, and mechanics indices calculation.

18. The system of claim 10, wherein the DENSE images of the tissue with blood suppression are utilized for quantitative assessment of biomarker parameters of tissue and organ, comprising one or more of mechanical properties parameters and time-resolved dynamic parameters.

\* \* \* \* \*